(12) United States Patent
Haas et al.

(10) Patent No.: US 7,579,106 B2
(45) Date of Patent: Aug. 25, 2009

(54) HERMETIC SEAL FOR A FLUID FILL HOLE AND RELATED METHOD FOR USE IN AN IMPLANTABLE ELECTROCHEMICAL CELL

(75) Inventors: David P. Haas, Brooklyn Park, MN (US); Jeffrey S. Lund, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 497 days.

(21) Appl. No.: 10/365,955

(22) Filed: Feb. 12, 2003

(65) Prior Publication Data

US 2004/0161666 A1    Aug. 19, 2004

(51) Int. Cl.
*H01M 2/02*    (2006.01)
(52) U.S. Cl. ......................................................... 429/80
(58) Field of Classification Search .................... 429/80, 429/52, 63, 89, 180, 181, 184; 204/275.1
See application file for complete search history.

(56) References Cited

U.S. PATENT DOCUMENTS

| | | | |
|---|---|---|---|
| 4,397,919 A * | 8/1983 | Ballard | ........................ 429/53 |
| 4,542,080 A | 9/1985 | Phillips et al. | |
| 4,544,078 A * | 10/1985 | Arenas et al. | ................ 429/163 |
| 5,776,632 A * | 7/1998 | Honegger | .................... 429/185 |
| 5,866,851 A | 2/1999 | Taylor et al. | |
| 6,040,082 A | 3/2000 | Haas et al. | |
| 6,844,106 B2 * | 1/2005 | Heller, Jr. | ..................... 429/80 |
| 2004/0062986 A1 * | 4/2004 | Aamodt et al. | ............... 429/181 |

* cited by examiner

*Primary Examiner*—Patrick Ryan
*Assistant Examiner*—Monique Wills

(57) ABSTRACT

An electrochemical cell (10) suitable for use in an implantable medical device (110) includes a case (12) and a cover (30) attached to the case. The cover (30) is formed of a first material and has an outer surface (41) and an inner surface (42) defining a thickness thereof. The cover (30) also has a fluid fill hole (34) formed therein. The fluid fill hole (34) has an outer diameter (44) at the outer surface and a smaller inner diameter (45) at the inner surface. A hermetic seal (62) is formed within the fluid fill hole (34) of a second material that is softer than the first material and that is deformed to assume the approximate shape of the fluid fill hole (34).

31 Claims, 5 Drawing Sheets

HERMETIC SEAL FOR A FLUID FILL HOLE AND RELATED METHOD FOR USE IN AN IMPLANTABLE ELECTROCHEMICAL CELL

TECHNICAL FIELD

This invention relates generally to electrochemical cells, and more particularly, to implantable electrochemical cells using liquid electrolytes or liquid catholytes.

BACKGROUND OF THE INVENTION

Electrochemical cells are commonly used in implantable medical devices. They are required to be small and to have a high energy per unit volume. Some of these cells use liquid electrolytes or liquid catholytes and these liquids are introduced into the battery case during manufacture using a fluid fill hole. The fluid fill hole is a small opening in the cover through which the fluid is injected. After the battery case has been filled with fluid, the hole is then hermetically sealed to prevent the fluid from escaping during the life of the battery.

There are several known hermetic sealing processes and they typically use both a primary seal and a secondary seal. The secondary seal provides a barrier between the fluid and escaping gas from the interior of the cell and the primary seal zone. This barrier is designed to eliminate possible contamination of the primary seal by electrolyte or catholyte liquid and vapor. The secondary seal is formed by fitting a plug of a suitable material such as metal, polymer, ceramic, or some combination snugly into the fluid fill hole. The primary seal is thereafter formed by fusing a metallic component which spans the fluid fill hole to the outside surface to provide a hermetic seal that is flush with the surface of the case. A known alternative uses a tube as the fluid fill hole. The tube is inserted into a hole in the battery enclosure, and when the fluid fill step is complete the tube is crimped and welded. The crimped tube protrudes from the surface and thus adds to the size of the cell.

These known hermetic seals suffer from several problems. First, all of the processes use space in addition to the cell case and cover. If the plug extends into the interior of the cell, then the design of the electrode is restricted and cell storage capacity is reduced. If the additional space is external the design of the device and other components in the implantable medical device may be affected and the overall size of the device will increase.

Second, the process of welding a metallic seal or crimped tube to form the primary seal produces undesirable heat. The heat produced by the welding process is thermally conducted through the fill hole hardware to the interior of the cell. This heat may damage thermally sensitive materials in close proximity to the fill hole hardware, and care must be taken to design electrodes that will not be damaged by the heat of the weld.

Third, the welding process may itself cause product failure. For all of the designs using a secondary seal, some electrolyte or catholyte material may adhere to surfaces not contained by the sealing materials and may emit sufficient vapors to contaminate the primary seal. These contaminated areas may exhibit themselves as blown welds during the fusion process.

Fourth, the final leak test used to detect blown welds may cause product failure. One such leak test uses a helium bombed glass bubble insertion step. The bubbles are placed between the outer surface of the secondary sealing materials and the inner surface of the primary sealing materials. However these bubbles may occasionally become entrapped in the primary seal zone. During the welding process, these bubbles may themselves also produce blown welds.

What is needed then is hermetic sealing process for a fluid fill hole of an electrochemical cell that overcomes these problems. Such a cell, an implantable medical device using it, and a process for manufacturing the cell are provided by the present invention, whose features and inventive elements will become more clearly understood from the following detailed description taken in conjunction with the accompanying drawings.

SUMMARY OF THE INVENTION

Accordingly the present invention provides, in one form, an electrochemical cell suitable for use in an implantable medical device. The electrochemical cell includes a case and a cover attached to the case. The cover is formed of a first material and has an outer surface and an inner surface defining a thickness thereof. The cover also has a fluid fill hole formed therein. The fluid fill hole has an outer diameter at the outer surface and a smaller inner diameter at the inner surface. A hermetic seal is formed within the fluid fill hole of a second material that is softer than the first material and that is deformed to assume the approximate shape of the fluid fill hole.

In another form the present invention provides an implantable medical device comprising a load circuit and an electrochemical cell coupled to the load circuit for supplying operating power thereto. The electrochemical cell includes a case and a cover attached to the case. The cover is formed of a first material and has an outer surface and an inner surface defining a thickness thereof. The cover also has a fluid fill hole formed therein. The fluid fill hole has an outer diameter at the outer surface and a smaller inner diameter at the inner surface. A hermetic seal is formed within the fluid fill hole of a second material that is softer than the first material and that is deformed to assume the approximate shape of the fluid fill hole.

In yet anther form the present invention provides a method for manufacturing an electrochemical cell. A fluid fill hole is formed in a cover of the electrochemical cell. The fluid fill hole extends from an outer surface to an inner surface of the cover. The fluid fill hole has an outer diameter at the outer surface and a smaller inner diameter at the inner surface. The electrochemical cell is filled with fluid through the fluid fill hole thereby to activate the electrochemical cell. A spherical ball is pressed into the fluid fill hole. A diameter of the spherical ball is between the outer diameter and the inner diameter of the fluid fill hole. The spherical ball is formed of a softer material than the cover, such that in response to being pressed the spherical ball deforms to assume the approximate shape of the fluid fill hole, thereby forming a hermetic seal.

BRIEF DESCRIPTION OF THE DRAWINGS

The following drawings are illustrative of particular embodiments of the invention and therefore do not limit the scope of the invention, but are presented to assist in providing a proper understanding. The drawings are not to scale and are intended for use in conjunction with the explanations in the following detailed description. The present invention will hereinafter be described in conjunction with the appended drawings, wherein like numerals denote like elements, and.

DETAILED DESCRIPTION OF EXEMPLARY EMBODIMENTS

The following description is exemplary in nature and is not intended to limit the scope, applicability, or configuration of the invention in any way. Rather the following description provides a convenient illustration for implementing exemplary embodiments of the invention. Various changes to the described embodiments may be made in the function and arrangements of the elements described herein without departing from the scope of the invention.

Figure 1:
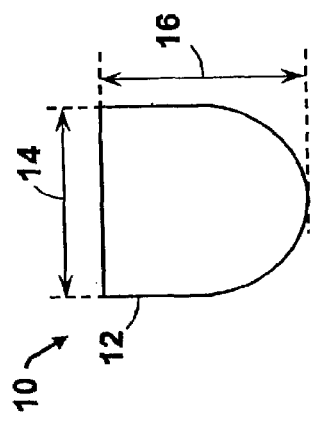
FIG. 1 illustrates a side view of an electrochemical cell suitable for use in an implantable medical device according to the present invention.

FIG. 1 illustrates a side view of an electrochemical cell 10 suitable for use in an implantable medical device according to the present invention. FIG. 1 shows cell 10 at the beginning of the manufacturing process. As can be seen from FIG. 1 cell 10 has a case 12 of a generally elongated semicircular shape. In this respect it preferably has a length 14 of about 1.074 inches and a height 16 of about 1.205 inches. In order to achieve a high energy per unit volume useful for an implantable medical device, electrochemical cell 10 is preferably formed with a solid anode and solid cathode using a liquid electrolyte. Many common electrolytes have relatively low evaporation points. A sufficient amount of the electrolyte may evaporate when exposed to the heat of a welding process to result in a blown weld. Such a blown weld jeopardizes the hermeticity of the cell. According to the present invention, however, a battery with liquid electrolyte or liquid catholyte can be manufactured without thermal welding as further described below.

Figure 2:
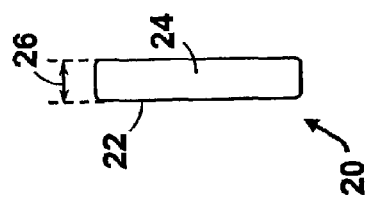
FIG. 2 illustrates a top view of the electrochemical cell of FIG. 1.

FIG. 2 illustrates a top view 20 of electrochemical cell 10 of FIG. 1, showing an outer perimeter 22 and an opening 24. Cell 10 has a width 26 of approximately 0.23 inches. During manufacturing of electrochemical cell 10 the anode and cathode are formed using conventional processes prior to insertion into the interior of cell 10.

Figure 3:
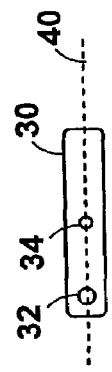
FIG. 3 illustrates a top view of a cover to be used with the electrochemical cell of FIG. 1.

FIG. 3 illustrates a top view of a cover 30 to be used with electrochemical cell 10 of FIG. 1. Cover 30 has a size and shape to fit within outer perimeter 22 and to be welded thereto. Cover 30 is formed with grade-2 or grade-3 titanium or other metal of similar hardness. Titanium has many properties that make it suitable for use in an implantable medical device, including the fact that it does not react with many common electrolytes, including the organic electrolyte used in cell 10. Cover 30 has two holes 32 and 34. Hole 32 is a feed-through hole adapted for a glass insulated wire anode that is welded to an anode grid made of etched foil and pressed into lithium. The cathode does not have a separate wire terminal but instead is a block pressed into a metal frame and welded to cover 30. After anode and cathode attachment the cover assembly is then slipped into opening 24 and welded onto case 12. Hole 34 is used as a fluid fill hole. As shown from the top view an axis 40 defines a cross section of fluid fill hole 34.

Figure 4:
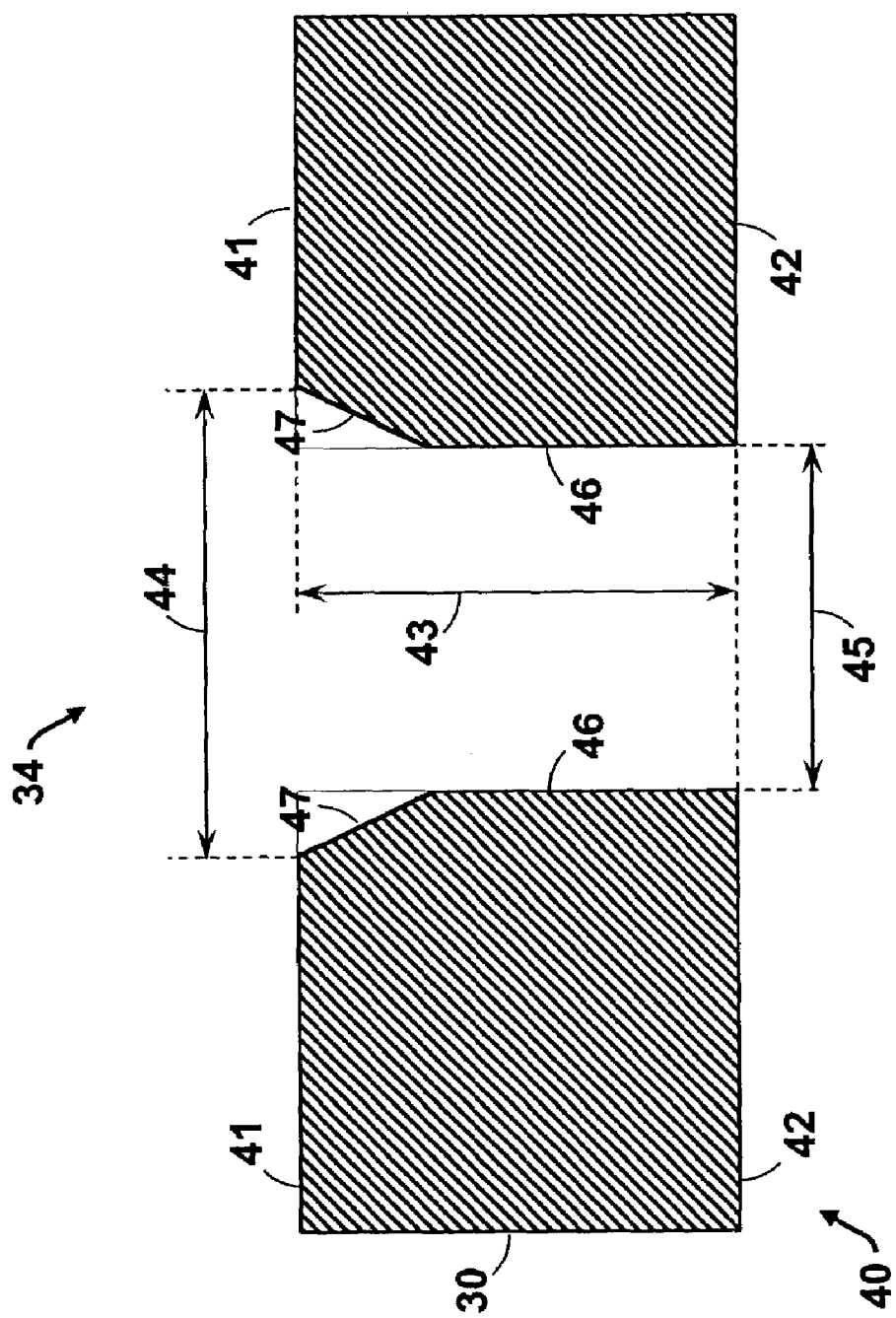
FIG. 4 illustrates a cross section of the fluid fill hole in the cover of FIG. 3.

FIG. 4 illustrates cross section 40 of fluid fill hole 34 in cover 30 of FIG. 3. As can be seen from FIG. 4 cover 30 has an outer surface 41 and an inner surface 42 defining a thickness 43 of cover 30, which is preferably about 0.320 inches. Fluid fill hole 34 can be formed as follows. First, a countersink lead-in is formed in cover 30 using a #0000 center drill with a 60° included angle to a depth of approximately 0.020 inches to form an outer diameter 44 having a size in the range of about 0.034 to about 0.038 inches. Next a through hole is formed by drilling into cover 30 concentrically with the lead-in, using a #70 or #71 cobalt steel drill having a bit size determining an inner diameter 45 of between approximately 0.0260 inches for a #71 drill and 0.0280 inches for a #70 drill. When the through hole drilling step is complete fluid fill hole 34 has a straight side wall 46 and a chamfer 47 near outer surface 41 such that hole 34 is wider near the outer surface.

The shape of fluid fill hole 34 is preferably slightly different from that shown in FIG. 4 to reduce the sharp edge between sidewall 46 and chamfer 47. The modification can be made in at least two ways. First, the edge could be radiused instead of chamfered using electrical discharge machining (EDM) processing. Second, fluid fill hole 34 could be tapered.

Figure 5:
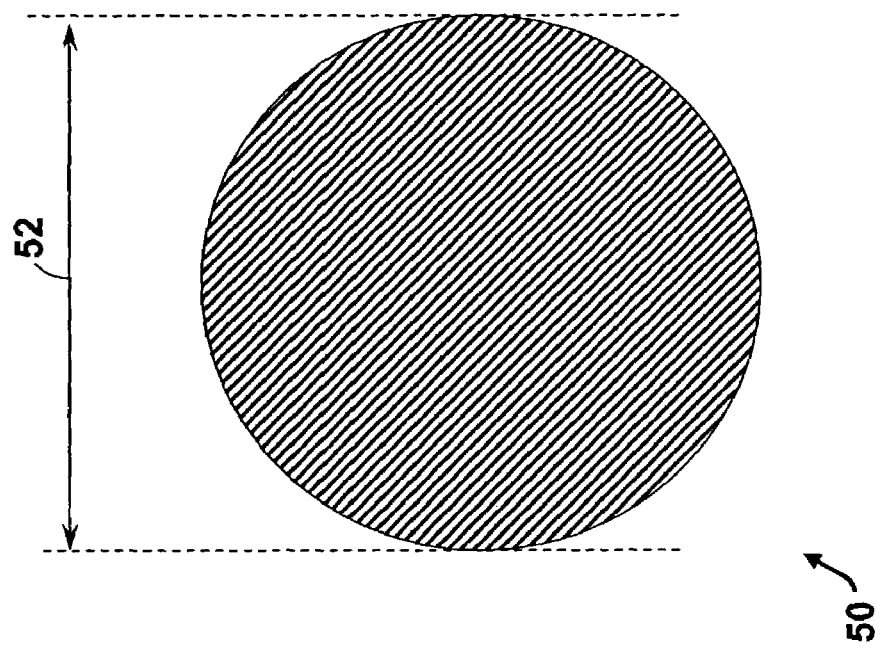
FIG. 5 illustrates a spherical ball for use in hermetically sealing the fluid fill hole of FIG. 4.

FIG. 5 illustrates a spherical ball 50 for use in hermetically sealing fluid fill hole 34 of FIG. 4. Spherical ball 50 is a grade 1 titanium ball having a diameter 52 of approximately $\frac{1}{32}^{nd}$ (0.03125) inch, which is less than outer diameter 44 but greater than inner diameter 45. Grade 1 titanium is a purer form of titanium than the grade 2 or grade 3 titanium used in cover 30 and thus spherical ball 50 is softer than cover 30. Then spherical ball 50 is pressed using approximately 75-85 pounds of force on a press fitted with a flat faced punch until the face of the punch bottoms out on surface 41.

Alternatively it is believed that commercially available 1 millimeter (mm.) titanium balls could be used in place of $\frac{1}{32}^{nd}$ inch ball 50. For use with such a ball outer diameter 45 must be slightly greater than 1 mm. and inner diameter 44 must be slightly less than 1 mm.

Figure 6:
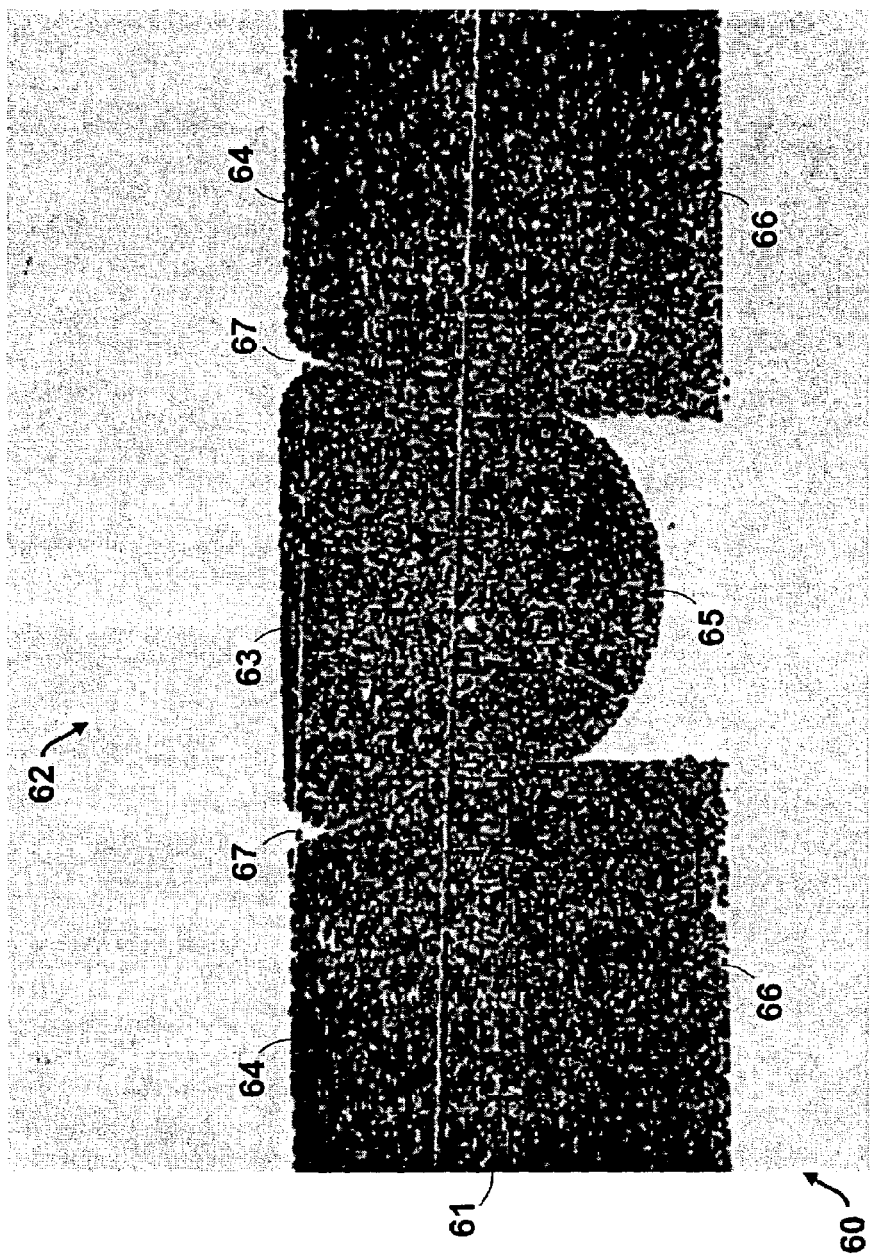
FIG. 6 illustrates a cross section of a hermetically sealed fluid fill hole.

FIG. 6 illustrates a cross section 60 of a finished cover 61 having a hermetically sealed fluid fill hole. As can be seen in FIG. 6 relatively soft spherical ball 50 deforms under the force of the press to assume the approximate shape of fluid fill hole 34. The resulting deformed ball 62 makes a hermetic seal and has a flat surface 63 that is substantially flush with an outer surface 64 of cover 61 and is thus exposed to an environment outward of the outer surface 64. Deformed ball 62 has an inner curved surface 65 that does not extend inward beyond an inner surface 66 of cover 61 into the interior of the cell. Inner curved surface 65 is shown exposed to the interior of the cell. The outer surface of the sealed cover is not continuous and has a small circular groove 67 caused by the failure of deformed ball 62 to completely fill the hole. Deformed ball 62 forms a "cold weld" that seals cover 61 hermetically. Fluid leakage was measured at less than $1 \times 10^{-7}$ cubic centimeters per second (cc/sec) at one standard atmosphere of helium, which is a sufficient hermetic seal for use in implantable medical devices.

Additional sealing steps can be used in conjunction with hermetic seal 62. For example, non-thermal welding can be used. Thus it is possible to sonically weld ball 50 to cover 30, either during or after insertion. It is also possible to use resistance welding during ball insertion or laser welding after insertion.

The hermetic seal described above overcomes the problems with other known hermetic seals. First the hermetic seal uses zero volume in addition to the cell case and cover. Deformed spherical ball 62 is substantially flush with the surface of the cover and does not extend from the inner surface of the cover inward into the interior of the cell. Second since there is no thermal welding step the hermetic seal avoids the problems associated with the heat of welding. Third, the hermetic seal eliminates additional steps required to create a secondary seal. Fourth no final leak test is required, avoiding additional failures caused by the leak test itself.

Figure 7:
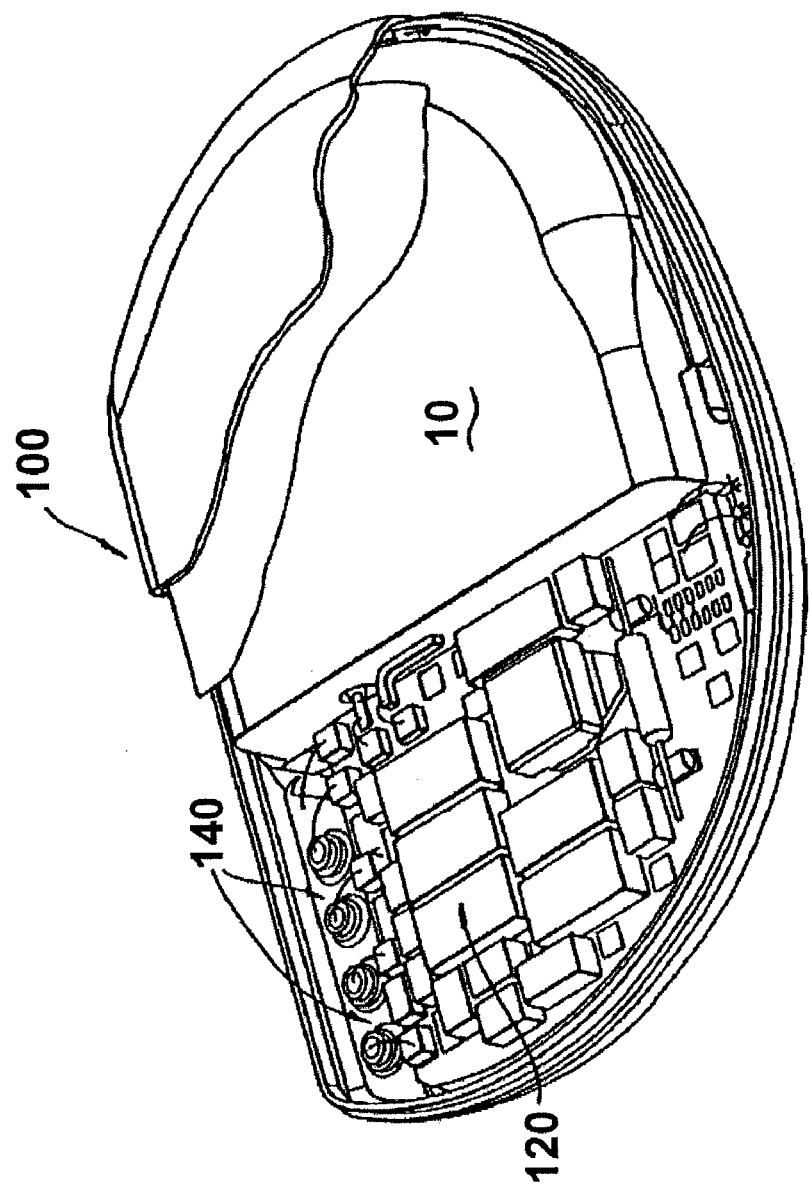
FIG. 7 illustrates a block diagram of an implantable medical device capable of using the electrochemical cell of FIG. 1 according to the present invention.

FIG. 7 illustrates a block diagram of an implantable medical device 100 using electrochemical cell 10 of FIG. 1 according to the present invention. Device 100 is one example of an implantable medical device which may use cell 10, namely a heart pacemaker. Device 100 is shown generically and includes cell 10, a load circuit 120, and a linearly arranged plurality of feedthroughs 140. A more complete description of the structure of device 100 can be found in U.S. Pat. No. 5,866,851, which is herein incorporated by reference in its entirety.

It should be apparent that for any type of implantable medical device it is important for the electrochemical cell to occupy as small a volume as possible and to store the maximum amount of energy to maximize cell life since implantation involves an invasive surgical procedure. Furthermore it is essential that liquid electrolyte or catholyte fluid be hermetically sealed because leaking fluid could damage the circuitry in the device. Thus cell 10 is useful in other types of implantable medical devices including stimulators, drug pumps, monitoring devices, and the like, and with various load circuits.

Note that while the hermetic seal and sealing process are especially suited for a cell to be used in an implantable medical device, they are also useful for other types of medical and commercial cells that are not intended for implantation. For example they can also be used to form a hermetic seal for other devices in which a fluid is added to a sealed container, such as capacitors using liquid electrolytes. They can also be used in a cover of a battery whose case has a different overall shape than the elongated semicircular shape shown in FIG. 1 above.

Furthermore various alternative materials may be used for the components. In other embodiments other cover and/or case materials such as aluminum, stainless steel, other metals, ceramics, polymers, and the like may be used. The important characteristic of the materials is that they be chosen such that the ball material be sufficiently softer than the cover so that it deforms in the presence of an applied force.

Various aspects of the cell manufacturing process may be altered as well. For example, the balls may be applied wet or dry. The profile of the fluid fill hole may also assume other shapes besides the countersunk (chamfered) shape described above, including tapered and radiused. Also the ball may be deformed using forces applied in varying manners including the application of a continuous force until the surface of the ball is flush with the surface of the cover, or by an impact press.

In the foregoing specification, the invention has been described with reference to specific embodiments. However, it may be appreciated that various modifications can be made without departing from the scope of the invention as set forth in the appended claims. Accordingly, the specification and figures are to be regarded as illustrative rather than as restrictive, and all such modifications are intended to be included within the scope of the present invention.

What is claimed is:

1. An electrochemical cell suitable for use in an implantable medical device comprising:
a case;
a cover attached to said case formed of a first material and having an outer surface and an inner surface defining a thickness thereof and having a fluid fill hole formed therein;
said fluid fill hole having an outer diameter at said outer surface and a smaller inner diameter at said inner surface; and
a single hermetic seal member formed within said fluid fill hole of a second material that is softer than said first material and that is deformed to assume the approximate shape of the fluid fill hole thereby forming a single hermetic seal between the first material and the second material, the single hermetic seal formed without a thermal weld, and the single hermetic seal member being exposed to an environment outward of the outer surface and exposed to an interior of the electrochemical cell.

2. The electrochemical cell of claim 1 wherein said hermetic seal member is further characterized as being substantially flush with said outer surface and not extending inward beyond said inner surface.

3. The electrochemical cell of claim 1 wherein said cover is welded to said case and the electrochemical cell further comprises fluid disposed within in an enclosure defined by said cover and said case.

4. The electrochemical cell of claim 3 wherein said fluid is characterized as being an electrolyte that activates the electrochemical cell.

5. The electrochemical cell of claim 1 wherein said hermetic seal member comprises titanium.

6. The electrochemical cell of claim 5 wherein said hermetic seal member comprises a deformed grade 1 titanium ball.

7. The electrochemical cell of claim 6 wherein said cover comprises a selected one of grade 2 titanium and grade 3 titanium.

8. The electrochemical cell of claim 1 wherein said cover includes a second hole for providing a connection to an electrode within the electrochemical cell.

9. The electrochemical cell of claim 8 wherein said electrode comprises one of an anode, a cathode and a neutrally charged layer.

10. An implantable medical device comprising:
a load circuit; and
an electrochemical cell coupled to said load circuit for supplying operating power thereto and comprising:
a case;
a cover attached to said case formed of a first material and having an outer surface and an inner surface defining a thickness thereof and having a fluid fill hole formed therein;
said fluid fill hole having an outer diameter at said outer surface and a smaller inner diameter at said inner surface; and
a single hermetic seal member formed within said fluid fill hole of a second material that is softer than said first material and that is deformed to assume the approximate shape of the fluid fill hole thereby forming a single hermetic seal between the first material and the second material, the single hermetic seal formed without a thermal weld, and the single hermetic seal member being exposed to an interior of the implantable medical device and exposed to an interior of the electrochemical cell.

11. The implantable medical device of claim 10 wherein said hermetic seal member is further characterized as being substantially flush with said outer surface and not extending inward beyond said inner surface.

12. The implantable medical device of claim 10 characterized as being a heart pacemaker.

13. The implantable medical device of claim 10 wherein said cover is welded to said case and the electrochemical cell further comprises fluid disposed within in an enclosure defined by said cover and said case.

14. The implantable medical device of claim 13 wherein said fluid is characterized as being an electrolyte that activates the electrochemical cell.

15. The implantable medical device of claim 10 wherein said hermetic seal member comprises titanium.

16. The implantable medical device of claim 15 wherein said hermetic seal member comprises a deformed grade 1 titanium ball.

17. The implantable medical device of claim 16 wherein said cover comprises a selected one of grade 2 titanium and grade 3 titanium.

18. The implantable medical device of claim 10 wherein said cover includes a second hole for providing a connection to an electrode within the electrochemical cell.

19. The implantable medical device of claim 18 wherein said electrode comprises one of an anode, a cathode and a neutrally charged layer.

20. A method for manufacturing an electrochemical cell comprising the steps of:
   forming a fluid fill hole in a cover of the electrochemical cell, said fluid fill hole extending from an outer surface to an inner surface of the cover and having an outer diameter at said outer surface and a smaller inner diameter at said inner surface;
   filling the electrochemical cell with fluid through said fluid fill hole thereby to activate the electrochemical cell; and
   pressing a spherical ball into said fluid fill hole, wherein a diameter of said spherical ball is between said outer diameter and said inner diameter of said fluid fill hole, said spherical ball being formed of a softer material than said cover, such that in response to said step of pressing said spherical ball deforms to assume the approximate shape of said fluid fill hole, thereby forming a hermetic seal, the hermetic seal formed without a thermal weld, and the single hermetic seal member being exposed to an environment outward of the outer surface and exposed to an interior of the electrochemical cell.

21. The method of claim 20 wherein said step of forming said fluid fill hole comprises the steps of:
   forming a lead-in near said outer surface; and
   forming a through hole substantially concentric with said lead-in and extending to said inner surface.

22. The method of claim 21 wherein said step of forming said lead-in comprises drilling.

23. The method of claim 21 wherein said step of forming said through hole comprises drilling.

24. The method of claim 20 wherein said step of forming said fluid fill hole comprises the step of forming a taper from said outer surface to said inner surface.

25. The method of claim 20 wherein said step of pressing said spherical ball comprises the step of pressing a spherical ball consisting essentially of titanium.

26. The method of claim 25 wherein said step of pressing said spherical ball consisting essentially of titanium comprises the step of pressing a grade-1 titanium ball.

27. The method of claim 26 wherein said step of forming said fluid fill hole comprises the step of forming a fluid fill hole extending from said outer surface to said inner surface of a cover consisting essentially of titanium.

28. The method of claim 27 wherein said step of forming said fluid fill hole comprises the step of forming said fluid fill hole extending from said outer surface to said inner surface of a cover formed of a selected one of grade-2 titanium and grade-3 titanium.

29. An electrochemical cell suitable for use in an implantable medical device comprising:
   a case;
   a cover attached to said case formed of a first material and having an outer surface and an inner surface defining a thickness thereof and having a fluid fill hole formed therein;
   said fluid fill hole having an outer diameter at said outer surface and a smaller inner diameter at said inner surface; and
   a single hermetic seal member formed within said fluid fill hole of a second material that is softer than said first material and that is deformed to assume the approximate shape of the fluid fill hole thereby forming a single hermetic seal between the first material and the second material, the single hermetic seal formed without a thermal weld, and the single hermetic seal member being exposed to an environment outward of the outer surface and exposed to an interior of the electrochemical cell;
   wherein said hermetic seal comprises a deformed grade 1 titanium ball and said cover comprises a selected one of grade 2 titanium and grade 3 titanium.

30. An electrochemical cell suitable for use in an implantable medical device comprising:
   a case;
   a cover attached to said case formed of a first material and having an outer surface and an inner surface defining a thickness thereof and having a fluid fill hole formed therein;
   said fluid fill hole having an outer diameter at said outer surface and a smaller inner diameter at said inner surface; and
   a single hermetic seal member formed within said fluid fill hole of a second material that is softer than said first material and that is deformed to assume the approximate shape of the fluid fill hole thereby forming a single hermetic seal between the first material and the second material, and the single hermetic seal member being exposed to an environment outward of the outer surface and exposed to an interior of the electrochemical cell.

31. An electrochemical cell suitable for use in an implantable medical device comprising:
   a case;
   a cover attached to said case formed of a first material and having an outer surface and an inner surface defining a thickness thereof and having a fluid fill hole formed therein;
   said fluid fill hole having an outer diameter at said outer surface and a smaller inner diameter at said inner surface; and
   a single hermetic seal member formed within said fluid fill hole of a second material that is softer than said first material and that is deformed to assume the approximate shape of the fluid fill hole thereby forming a single hermetic seal between the first material and the second material, and the single hermetic seal member being exposed to an environment outward of the outer surface and exposed to an interior of the electrochemical cell;
   wherein said hermetic seal comprises a deformed grade 1 titanium ball and said cover comprises a selected one of grade 2 titanium and grade 3 titanium.

* * * * *

UNITED STATES PATENT AND TRADEMARK OFFICE
CERTIFICATE OF CORRECTION

PATENT NO. : 7,579,106 B2
APPLICATION NO. : 10/365955
DATED : August 25, 2009
INVENTOR(S) : Haas et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 682 days.

Signed and Sealed this

Fourteenth Day of September, 2010

David J. Kappos
*Director of the United States Patent and Trademark Office*